(12) United States Patent
Hindrichs et al.

(10) Patent No.: US 9,101,338 B2
(45) Date of Patent: Aug. 11, 2015

(54) SOFT BODY TISSUE REMODELING METHODS AND APPARATUS

(75) Inventors: Paul J. Hindrichs, Plymouth, MN (US);
Steven D Kruse, St. Michael, MN (US);
Todd A Krinke, Buffalo, MN (US);
Michael P. Brenzel, St. Paul, MN (US);
Kenton J. Zehr, Pittsburgh, PA (US);
Paul Thompson, Minnetonka, MN (US);
Theodore P. Dale, Minneapolis, MN (US); David M. Costello, Waconia, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 1833 days.

(21) Appl. No.: 11/800,363

(22) Filed: May 3, 2007

(65) Prior Publication Data

US 2007/0282375 A1 Dec. 6, 2007

Related U.S. Application Data

(60) Provisional application No. 60/797,615, filed on May 3, 2006.

(51) Int. Cl.
*A61B 17/04* (2006.01)
*A61B 17/00* (2006.01)
(Continued)

(52) U.S. Cl.
CPC ....... *A61B 17/00234* (2013.01); *A61B 17/0401* (2013.01); *A61B 17/064* (2013.01); *A61B 17/068* (2013.01); *A61F 2/2451* (2013.01); *A61B 17/0487* (2013.01); *A61B 2017/00243* (2013.01); *A61B 2017/0409* (2013.01); *A61B 2017/0414* (2013.01); *A61B 2017/0441* (2013.01);
(Continued)

(58) Field of Classification Search
CPC .......... A61B 17/0401; A61B 17/0487; A61B 17/064; A61B 17/068; A61B 2017/0414; A61B 2017/0441; A61B 2017/0454; A61B 2017/0496; A61B 2017/0648; A61F 2/2451
USPC ......... 606/232, 216, 264–275, 228, 300–320; 623/23.72
See application file for complete search history.

(56) References Cited

U.S. PATENT DOCUMENTS 5,201,734 A * 4/1993 Cozad et al. .................... 606/62
5,626,613 A 5/1997 Schmieding
(Continued)

FOREIGN PATENT DOCUMENTS

WO WO 00/44313 8/2000
WO WO 00/60995 10/2000
(Continued)

*Primary Examiner* — Alexander Orkin
(74) *Attorney, Agent, or Firm* — Marshall Gerstein & Borun LLP

(57) ABSTRACT

An implant structure for use in pulling two soft body tissue areas closer together in a patient (e.g., two points along or adjacent to the patient's mitral valve annulus) includes at least two tissue anchor structures that are respectively implantable into the two tissue areas. A tether structure links the two tissue anchors and can be shortened and held in that condition by a cinch structure. Bracing structures are used between the anchors and the tether to help keep the longitudinal axes of the anchors transverse to the tether axis even when the tether is under tension. The tether may be sheathed in a cushioning sleeve to help protect adjacent tissue from erosion by the tether.

24 Claims, 11 Drawing Sheets

(51) Int. Cl.
   *A61B 17/064* (2006.01)
   *A61B 17/068* (2006.01)
   *A61F 2/24* (2006.01)

(52) U.S. Cl.
   CPC . *A61B2017/0454* (2013.01); *A61B 2017/0496* (2013.01); *A61B 2017/0648* (2013.01); *A61B 2017/0649* (2013.01)

(56) References Cited

U.S. PATENT DOCUMENTS

| | | | |
|---|---|---|---|
| 5,728,116 A * | 3/1998 | Rosenman | 606/151 |
| 5,785,713 A | 7/1998 | Jobe | |
| 5,843,126 A * | 12/1998 | Jameel | 606/220 |
| 6,182,664 B1 | 2/2001 | Cosgrove | |
| 6,210,432 B1 | 4/2001 | Solem et al. | |
| 6,402,781 B1 | 6/2002 | Langberg et al. | |
| 6,537,314 B2 | 3/2003 | Langberg et al. | |
| 6,569,198 B1 | 5/2003 | Wilson et al. | |
| 6,656,221 B2 | 12/2003 | Taylor et al. | |
| 6,676,702 B2 | 1/2004 | Mathis | |
| 6,702,826 B2 | 3/2004 | Liddicoat et al. | |
| 6,706,065 B2 | 3/2004 | Langberg et al. | |
| 6,709,456 B2 | 3/2004 | Langberg et al. | |
| 6,769,434 B2 | 8/2004 | Liddicoat et al. | |
| 6,790,231 B2 | 9/2004 | Liddicoat et al. | |
| 6,793,673 B2 | 9/2004 | Kowalsky et al. | |
| 6,797,001 B2 | 9/2004 | Mathis et al. | |
| 6,800,090 B2 | 10/2004 | Alferness et al. | |
| 6,810,882 B2 | 11/2004 | Langberg et al. | |
| 6,824,562 B2 | 11/2004 | Mathis et al. | |
| 7,186,262 B2 * | 3/2007 | Saadat | 606/232 |
| 7,431,726 B2 * | 10/2008 | Spence et al. | 606/151 |
| 7,753,924 B2 * | 7/2010 | Starksen et al. | 606/151 |
| 2001/0018611 A1 | 8/2001 | Solem et al. | |
| 2001/0041821 A1 | 11/2001 | Wilk | |
| 2001/0044568 A1 | 11/2001 | Langberg et al. | |
| 2001/0047174 A1 * | 11/2001 | Donno et al. | 606/73 |
| 2002/0016628 A1 | 2/2002 | Langberg et al. | |
| 2002/0042621 A1 | 4/2002 | Liddicoat et al. | |
| 2002/0042651 A1 | 4/2002 | Liddicoat et al. | |
| 2002/0055742 A1 * | 5/2002 | Lieberman | 606/73 |
| 2002/0095167 A1 | 7/2002 | Liddicoat et al. | |
| 2002/0103532 A1 | 8/2002 | Langberg et al. | |
| 2002/0103533 A1 | 8/2002 | Langberg et al. | |
| 2002/0169502 A1 | 11/2002 | Mathis | |
| 2002/0183835 A1 | 12/2002 | Taylor et al. | |
| 2002/0183836 A1 | 12/2002 | Liddicoat et al. | |
| 2002/0183837 A1 | 12/2002 | Streeter et al. | |
| 2002/0183838 A1 | 12/2002 | Liddicoat et al. | |
| 2002/0183841 A1 | 12/2002 | Cohn et al. | |
| 2003/0013567 A1 | 1/2003 | Kern et al. | |
| 2003/0069636 A1 | 4/2003 | Solem et al. | |
| 2003/0078465 A1 | 4/2003 | Pai et al. | |
| 2003/0083538 A1 | 5/2003 | Adams et al. | |
| 2003/0105520 A1 | 6/2003 | Alferness et al. | |
| 2003/0130730 A1 | 7/2003 | Cohn et al. | |
| 2003/0130731 A1 | 7/2003 | Vidlund et al. | |
| 2003/0135267 A1 | 7/2003 | Solem et al. | |
| 2003/0144697 A1 | 7/2003 | Mathis et al. | |
| 2003/0171776 A1 | 9/2003 | Adams et al. | |
| 2003/0171806 A1 | 9/2003 | Mathis et al. | |
| 2003/0181928 A1 | 9/2003 | Vidlund et al. | |
| 2003/0212453 A1 | 11/2003 | Mathis et al. | |
| 2003/0225454 A1 | 12/2003 | Mathis et al. | |
| 2003/0236569 A1 | 12/2003 | Mathis et al. | |
| 2004/0010305 A1 | 1/2004 | Alferness et al. | |
| 2004/0019377 A1 | 1/2004 | Taylor et al. | |
| 2004/0034380 A1 | 2/2004 | Woolfson et al. | |
| 2004/0039443 A1 | 2/2004 | Solem et al. | |
| 2004/0049190 A1 * | 3/2004 | Biedermann et al. | 606/61 |
| 2004/0073302 A1 | 4/2004 | Rourke et al. | |
| 2004/0102839 A1 | 5/2004 | Cohn et al. | |
| 2004/0102840 A1 | 5/2004 | Solem et al. | |
| 2004/0102841 A1 | 5/2004 | Langberg et al. | |
| 2004/0111095 A1 | 6/2004 | Gordon et al. | |
| 2004/0127906 A1 * | 7/2004 | Culbert et al. | 606/72 |
| 2004/0127980 A1 | 7/2004 | Kowalsky et al. | |
| 2004/0133220 A1 | 7/2004 | Lashinski et al. | |
| 2004/0133240 A1 | 7/2004 | Adams et al. | |
| 2004/0138744 A1 | 7/2004 | Lashinski et al. | |
| 2004/0153052 A1 | 8/2004 | Mathis | |
| 2004/0153147 A1 | 8/2004 | Mathis | |
| 2004/0158321 A1 | 8/2004 | Reuter et al. | |
| 2004/0176840 A1 | 9/2004 | Langberg et al. | |
| 2004/0186566 A1 * | 9/2004 | Hindrichs et al. | 623/2.37 |
| 2004/0193260 A1 | 9/2004 | Alferness et al. | |
| 2004/0210240 A1 | 10/2004 | Saint | |
| 2004/0220654 A1 | 11/2004 | Mathis et al. | |
| 2004/0236419 A1 | 11/2004 | Milo | |
| 2004/0243228 A1 | 12/2004 | Kowalsky et al. | |
| 2004/0249452 A1 | 12/2004 | Adams et al. | |
| 2004/0254600 A1 | 12/2004 | Zarbatany et al. | |
| 2004/0260317 A1 * | 12/2004 | Bloom et al. | 606/151 |
| 2005/0004667 A1 | 1/2005 | Swinford et al. | |
| 2005/0080416 A1 * | 4/2005 | Ryan et al. | 606/61 |
| 2005/0085815 A1 * | 4/2005 | Harms et al. | 606/61 |
| 2005/0177154 A1 * | 8/2005 | Moumene et al. | 606/61 |
| 2005/0182409 A1 * | 8/2005 | Callahan et al. | 606/72 |
| 2005/0203514 A1 * | 9/2005 | Jahng et al. | 606/61 |
| 2006/0058817 A1 | 3/2006 | Starksen et al. | |
| 2006/0282080 A1 * | 12/2006 | Albert et al. | 606/61 |
| 2007/0049942 A1 | 3/2007 | Hindrichs et al. | |
| 2008/0033232 A1 * | 2/2008 | Catanese et al. | 600/29 |

FOREIGN PATENT DOCUMENTS

| | | |
|---|---|---|
| WO | WO 01/28455 | 4/2001 |
| WO | WO 01/50985 | 7/2001 |
| WO | WO 01/54618 | 8/2001 |
| WO | WO 02/00099 | 1/2002 |
| WO | WO 02/01999 | 1/2002 |
| WO | WO 02/05888 | 1/2002 |
| WO | WO 02/19951 | 3/2002 |
| WO | WO 02/47539 | 6/2002 |
| WO | WO 02/053206 | 7/2002 |
| WO | WO 02/062263 | 8/2002 |
| WO | WO 02/062408 | 8/2002 |
| WO | WO 02/076284 | 10/2002 |
| WO | WO 02/078576 | 10/2002 |
| WO | WO 02/096275 | 12/2002 |
| WO | WO 03/015611 | 2/2003 |
| WO | WO 03/034947 | 5/2003 |
| WO | WO 03/055417 | 7/2003 |
| WO | WO 03/059198 | 7/2003 |
| WO | WO 03/088809 | 10/2003 |
| WO | WO 03/088873 | 10/2003 |
| WO | WO 2004/002290 | 1/2004 |
| WO | WO 2004/021893 | 3/2004 |
| WO | WO 2004/043265 | 5/2004 |
| WO | WO 2004/043293 | 5/2004 |
| WO | WO 2005/102181 | 11/2005 |

* cited by examiner

SOFT BODY TISSUE REMODELING METHODS AND APPARATUS

This application claims the benefit of U.S. provisional patent application No. 60/797,615, filed May 3, 2006, which is hereby incorporated by reference herein in its entirety.

BACKGROUND OF THE INVENTION

There is considerable interest in being able to reshape certain aspects of the mitral valve of certain patients in order to improve the functioning of that valve (e.g., to improve closure of the valve leaflets and thereby reduce or eliminate mitral regurgitation). Prior Hindrichs et al. U.S. patent application publications 2004-0186566 and 2007-0049942 show various techniques for doing this on the basis of relatively low invasiveness of the patient's body (e.g., percutaneously via catheter or catheter-like instrumentation). An illustrative approach shown in those prior patent applications is to drive a first screw-type anchor or a first pair of such anchors through the wall of the patient's coronary sinus and into adjacent heart muscle tissue that is in turn at or near a first point along the annulus of the mitral valve. A second screw-type anchor or a second pair of such anchors may be driven into the wall of the right atrium outside the ostium of the coronary sinus and at or adjacent to another point along the annulus of the mitral valve. A tether structure extends between the two anchor structures. The length of this tether structure can be shortened. This shortens the distance between the two anchor structures, which in turn shortens the length of the mitral valve annulus in this vicinity. Shortening the mitral valve annulus in this way can be beneficial to mitral valve performance (e.g., by improving the ability of the mitral valve leaflets to close and prevent undesirable blood regurgitation through the mitral valve).

Improvements to make apparatus of the type described above simpler and easier to use and capable of giving better results are always being sought.

SUMMARY OF THE INVENTION

An implant assembly in accordance with the invention may include two screw-type tissue anchor structures that are linked by a tether member. To help keep the longitudinal axes of the anchors transverse to the longitudinal axis of the tether, even when the tether is under tension between the anchors, bracing structures are used between the tether and the anchors. For example, such a bracing structure may work as follows: The bracing structure may be substantially rigid and may be substantially aligned with the longitudinal axis of the tether extending to the other (remotely located) anchor in the system. The bracing structure also preferably extends along the tether for a predetermined distance that extends from the associated anchor toward the other anchor. When tension in the tether tries to tip an anchor toward the other anchor, the tether tension force induces a force couple or moment that the associated bracing structure applies to the anchor to counteract the tipping motion. All of this structure can be delivered into patient piecemeal and via catheter or catheter-like instrumentation so that the implantation process can be performed at a remote location in the patient with relatively low invasiveness of the patient's body.

A possible further aspect of the invention is the provision of a cushioning sleeve around the tether between the tissue anchors. This sleeve can be joined to one of the bracing structures for delivery with that bracing structure in order to reduce the number of separate steps required in the implantation process.

A cinch structure may be deployed onto the tether structure to maintain desired spacing between the tissue anchors. Another possible aspect of the invention is to combine the cinch structure and a bracing structure, again to reduce the number of separate steps required in the implantation process.

Further features of the invention, its nature and various advantages, will be more apparent from the accompanying drawings and the following detailed description.

DETAILED DESCRIPTION

Above-mentioned U.S. patent applications 2004-0186566 and 2007-0049942 provide good background and context for the present invention. It will, therefore be assumed that this background and context information is known to the reader of this disclosure, and that this information does not have to be repeated in full in the present disclosure. Rather, the present disclosure will begin with that prior information as an assumedly known starting point. The following detailed discussion will begin with primary emphasis on an illustrative embodiment of an implant in accordance with the invention. Later, additional attention will be given to illustrative instrumentation in accordance with the invention for delivering and implanting this type of implant structure into a patient, especially in a low-invasiveness way.

Figure 1:
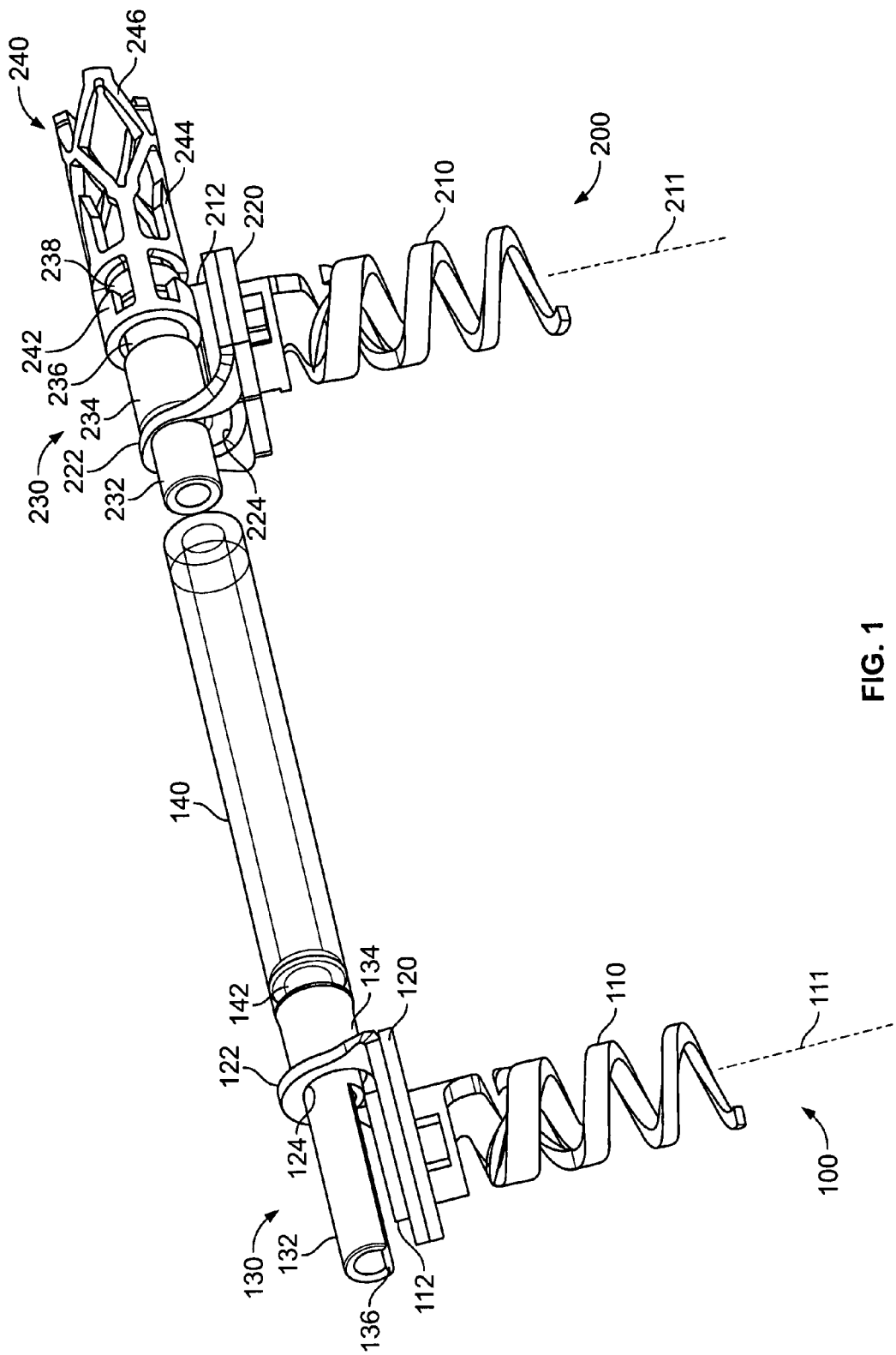
FIG. 1 is a simplified perspective or isometric view of an illustrative embodiment of certain components in accordance with the invention.

FIG. 1 shows, toward the left, an illustrative embodiment of a distal tissue anchor structure 100 in accordance with the present invention. As in the prior applications, distal tissue anchor structure is designed for percutaneous delivery into a patient's coronary sinus, where the screw-like, tissue-penetrating part 110 of that anchor structure will be driven through the wall of the coronary sinus and into adjacent heart muscle tissue that is in turn adjacent a point along the annulus of the patient's mitral valve. (An especially preferred location for distal anchor 100 is proximal to the point at which the coronary sinus crosses the circumflex artery and near the P2/P3 segment(s) of the posterior leaflet of the mitral valve. See FIG. 20 and the discussion thereof later in this specification.) When this is being done, collar structure 120 is around the head 112 of tissue-penetrating portion 110, but the collar is rotatable about the longitudinal axis 111 of portion 110. Although not shown in FIG. 1 (see, instead, FIG. 2), the distal end 302 of a flexible tether member 300 is attached to collar 120 at or near the point where collar 120 has an apertured portion 122 that extends up above the head 112 of portion 110. Also when portion 110 is being driven into tissue, none of the other elements that are shown in FIG. 1 (except collar 120) are present in the patient. As in the other above-mentioned patent applications, anchor 110 is driven from inside the patient's coronary sinus, substantially perpendicular to the inner wall surface of the coronary sinus, through the wall of the coronary sinus, and into adjacent heart muscle tissue as mentioned a few sentences earlier. The drive for anchor 110 can be similar to anchor drives shown in the other above-mentioned applications. Again, the instrumentation for delivering collar 120 and anchor 110, and driving the anchor, is preferably catheter or catheter-like apparatus.

Figure 2:
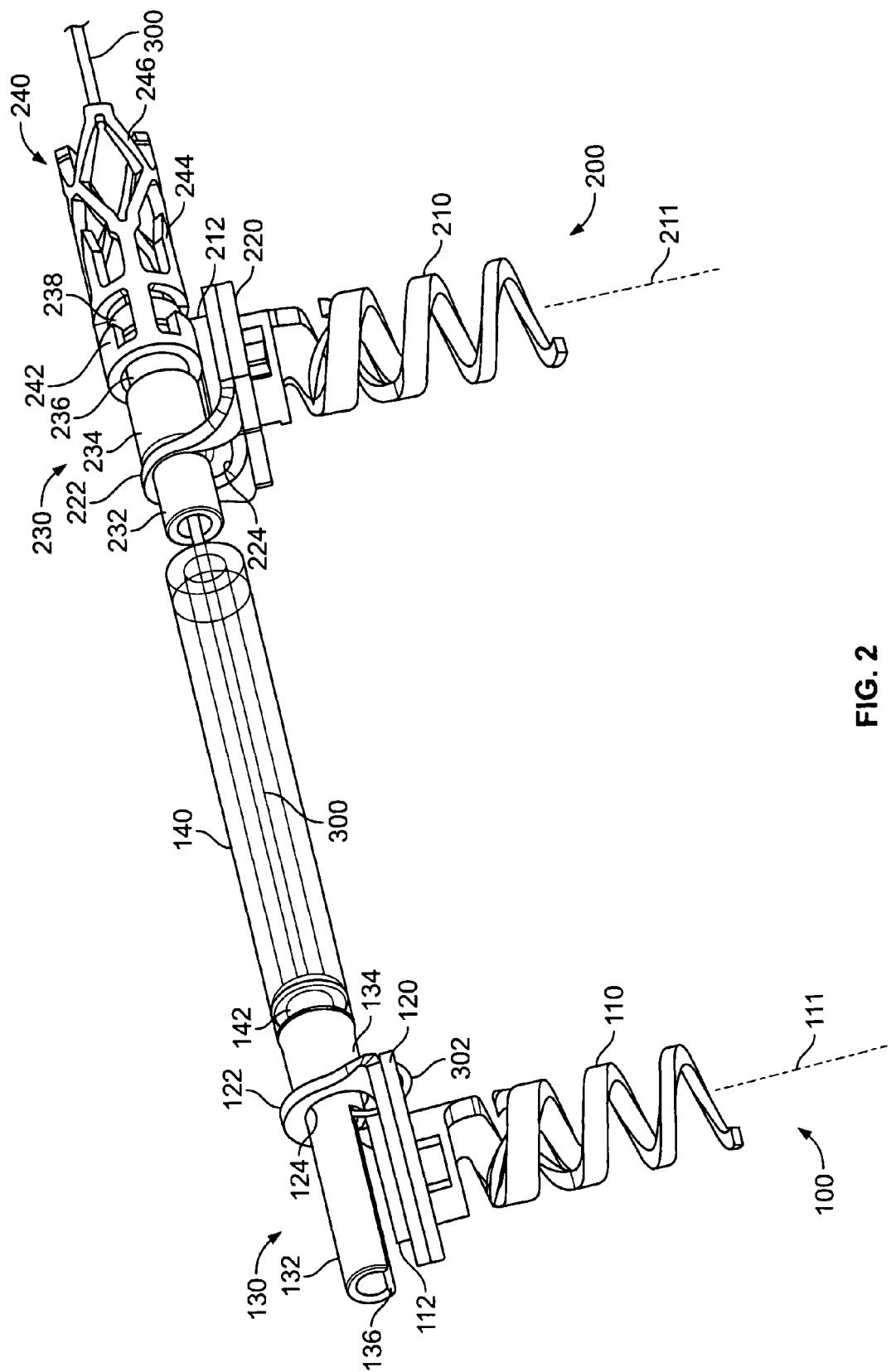
FIG. 2 is similar to FIG. 1, but with another component added.

When anchor 110 has been driven (as described above) far enough that collar 120 bears on the inner surface of the coronary sinus wall, driving of the anchor is stopped and the anchor is released from its drive. The apparatus that was used to drive anchor 110 can be withdrawn from the patient, and apparatus for the next phase of the procedure can be inserted into the patient in its place. It will be remembered that, as shown in FIG. 2, a tether member 300 extends (in the proximal direction) from collar 120 near apertured extension 122. A proximal continuation of this tether structure extends all the way out of the patient. Thus the next-phase of the apparatus can be introduced into the patient along this tether and its proximal extension. A small amount of proximal tension on the tether and its proximal extension can be used to keep collar 120 rotationally oriented on anchor 110 so that apertured extension 122 is toward the proximal side of the anchor.

The instrumentation for the next phase of the procedure is again preferably catheter or catheter-like instrumentation. This instrumentation has at its distal end an element 130 that may be referred to as a bracing or bushing structure. Bushing 130 (which is substantially rigid) is large enough to fit loosely around the above-mentioned tether member 300 and its proximal extension. Accordingly, this is the manner in which bushing 130 is fed into the patient (i.e., with the bushing around the tether structure). A distal portion 132 of bushing 130 has a smaller outer circumference than a proximal portion 134 of the bushing. The distal portion 132 of bushing 130 also has a longitudinal slot 136 that is wide enough to permit tether member 300 to extend laterally out of the bushing to the tether's attachment point 302 on collar 120. The distal portion 132 of bushing 130 is also small enough to pass easily through an aperture 124 in the apertured portion 122 of collar 120. However, the larger proximal portion 134 of bushing 130 is too large to pass through aperture 124. Accordingly, when pushed distally into the patient as described above, bushing 130 comes to rest against apertured portion 122 as shown in FIG. 1. Note that in this condition of the apparatus, the distal portion 132 of bushing 130 preferably extends across anchor head 112 and in close proximity thereto. A proximal portion of bushing 130 extends in the proximal direction along tether 300 for some distance from apertured portion 122. As will be shown in more detail later in this specification, these features help to keep the longitudinal axis 111 of implanted anchor 110 substantially perpendicular (or at least generally transverse) to the longitudinal axis of tether 300, even when the tether is pulling on structure 100 parallel to the surface of the tissue into which structure 100 has been implanted. Keeping anchor axis 111 substantially perpendicular (or at least transverse) to the tether axis counteracts what would otherwise be the tendency of anchor 110 to tip toward alignment with the tether axis when pulled on by the tether. Anchor 110 holds tissue more securely (i.e., the anchor is less likely to pull out of the tissue) when thus kept perpendicular or at least transverse to the tether axis.

Preferably attached to the proximal portion of bushing 130 is the distal end of an elongated sleeve structure 140 (shown as though transparent in FIG. 1). Sleeve 140 is preferably large enough to pass loosely around the above-mentioned tether member 300. Sleeve 140 is preferably flexible and relatively soft. Its primary purpose is to provide cushioning between tether member 300 and tissue structures that the tether member could otherwise come into contact with between distal anchor structure 100 and proximal anchor structure 200. Sleeve 140 acts as stress (or strain) relief by effectively increasing the diameter of the tether and thereby distributing the force applied to the tissue over a larger area. Sleeve 140 is preferably long enough to extend all the way along the tether member between implanted anchor structures 100 and 200; and because the distance between implanted structures 100 and 200 can be changed as part of the procedure, sleeve 140 is preferably elastic in the axial direction. This means that if the distance between implanted structures 100 and 200 decreases, sleeve 140 elastically shortens by a corresponding amount. Conversely, if the distance between implanted structures 100 and 200 increases again, sleeve 140 elastically lengthens by a corresponding amount so that the entire length of the tether between implanted structures 100 and 200 remains covered by sleeve 140. Illustrative materials for, and constructions of, sleeve 140 are described later in this specification. Sleeve 140 may include one or more radiologically visible markers 142. For example, it may be desirable to have such a marker near each end of the sleeve to help make sure that the sleeve does in fact extend all the way along the tether between anchor structures 100 and 200 during the implant procedure.

It is preferred to attach the distal end of sleeve 140 to bushing 130 because in this way delivering bushing 130 into the patient also pulls sleeve 140 into the patient. This saves separate delivery of sleeve 140. However, such attachment of components 130 and 140 is not essential, and they can instead be separate, with separate delivery of the sleeve being performed after delivery of bushing 130.

After structures 130 and 140 have been delivered into the patient as described above, the instrumentation used in the delivery of those components is withdrawn from the patient. The next step is to implant the screw-like, tissue-penetrating part 210 and collar structure 220 of proximal tissue anchor structure 200. As described in the other above-mentioned patent applications, a preferred location for implanting structure 200 is in the right atrium outside the ostium of the coronary sinus and toward the tricuspid valve. Additional considerations that may be applied to the proximal anchor location will be found in the other above-mentioned patent applications and need not be expressly repeated here. See also FIG. 20 and the later discussion of that FIG. herein.

The construction of elements 210 and 220 may be similar to the construction of elements 110 and 120, except that collar structure 220 does not need an attachment point for tether member 300. Components 210 and 220 are delivered into the patient with tether member 300 passing through the aperture 224 in the apertured portion 222 of collar 220. When components 210 and 220 have reached the desired location in the patient, anchor 210 is driven into tissue of the patient substantially perpendicular to the surface of that tissue. As mentioned above, this may involve driving anchor 210 into the wall of the patient's right atrium outside the ostium of the coronary sinus. The proximal end of sleeve 140 should be at or close to the apertured portion 222 of collar 220 that stands up above the head 212 of anchor 210.

After anchor 210 has been driven (with collar structure 220 rotatably mounted around its head), the instrumentation used for delivering and driving that anchor is withdrawn from the patient. The next step is delivery of components 230 and 240 into the patient.

Component 230 is another bracing or bushing structure. Component 240 is a cinch structure. Both of these structures go into the patient around tether member 300 and its proximal extension. Bushing 230 fits loosely around the tether. Cinch 240 initially fits loosely around the tether (on delivery instrumentation), but can be deployed to grip the tether. Components 230 and 240 are preferably connected together so that one delivery step can be used to deliver both of them. This is not essential, however, and these elements could instead be separate and therefore delivered separately, one after another by separate delivery means. Connecting them together (as in the FIG. 1 embodiment) has the advantage of reducing the required number of delivery steps and eliminating some separate delivery instrumentation. Further details of bushing 230 will be discussed next, and then further details of cinch 240 will be discussed.

Bushing 230 has a distal-most section 232 that is small enough in circumference to pass easily through the aperture 224 in the apertured portion 222 of collar 220 that stands up above the head 212 of anchor 210. After passing through aperture 224, the distal portion 232 preferably extends for some distance along tether 300 distal of apertured portion 222. The distal end of bushing 230 should either be received in or should abut or nearly abut the proximal end of sleeve 140. Just proximal of section 232, bushing 230 has another section 234 that has a larger circumference. In particular, section 234 is too large to pass through aperture 224. Proximal of section 234, bushing 230 may include features that facilitate interconnecting bushing 230 and cinch 240. For example, proximal of section 234, bushing 230 may have a section 236 of reduced circumference, and then an even more proximal section 238 of enlarged circumference. The distal portion of cinch 240 can fit over bushing sections 236 and 238, and then cinch fingers 242 can be deflected radially inwardly between enlarged bushing sections 234 and 238 to substantially prevent components 230 and 240 from thereafter moving axially relative to one another. Note that proximal portions (e.g., 234) of bushing 230 pass over the head 212 of anchor 210 in close proximity thereto. This fact, combined with portion 232 of bushing 230 passing through and distally beyond aperture 224, helps keep the longitudinal axis 211 of implanted anchor 210 substantially perpendicular (or at least generally transverse) to the longitudinal axis of tether 300 between structures 100 and 200, even when that length of the tether is under tension. In other words, these structural features (i.e., bushing 230 passing through and distally beyond aperture 222, as well as over the head 212 of anchor 210) help prevent implanted anchor 210 from tipping into alignment with the tether running from structure 200 toward structure 100. Anchor 210 is less likely to pull out of the tissue into which it has been driven if it can thus be kept transverse to (ideally substantially perpendicular to) the tether axis along which the tether is applying force to it.

Turning now to cinch structure 240, distal features 242 of that structure have already been described in connection with bushing structure 230. The proximal features can be similar to what has been described for a cinch structure in the latter of the two prior applications. In particular, when released from the condition shown in FIG. 1, the free ends of proximally directed prongs 244 incline inwardly to engage tether member 300 and prevent the cinch from moving proximally relative to the tether member. This holds anchor structures 100 and 200 at the desired spacing from one another along the tether member extending between structures 100 and 200. In addition, the cinch features like 246 that are proximal of prongs 244 also collapse inwardly onto the tether member. This helps counteract any tendency of the tether to unravel when it is subsequently cut proximal to cinch 240.

FIG. 2 is generally similar to FIG. 1, except that it additionally shows tether member 300. In particular, FIG. 2 shows that the distal end 302 of the tether is looped through an aperture in collar structure 120 to secure the tether to that collar structure. From there, tether 300 runs proximally through the proximal portion 134 of bushing structure 130, through sleeve structure 140, through bushing structure 230, and through cinch structure 240.

Figure 3:
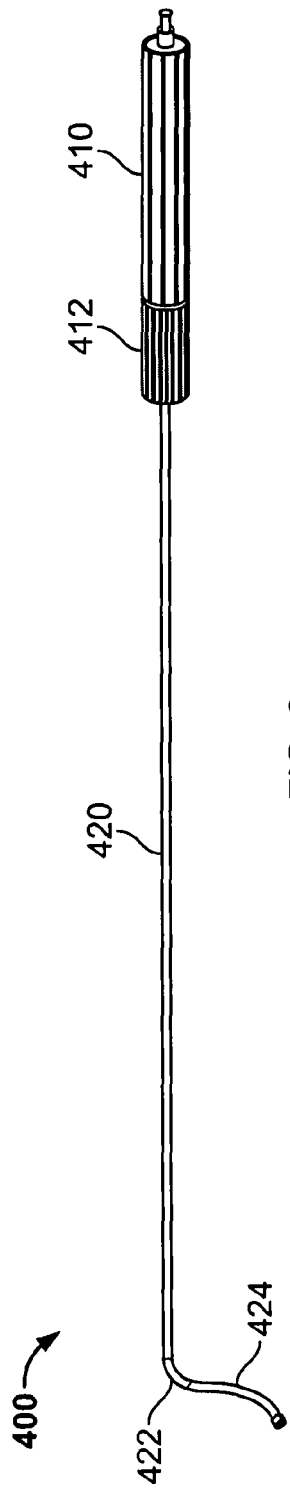
FIG. 3 is a simplified perspective or isometric view of an illustrative embodiment of some instrumentation and apparatus that may be constructed and employed in accordance with the invention.
Figure 4:
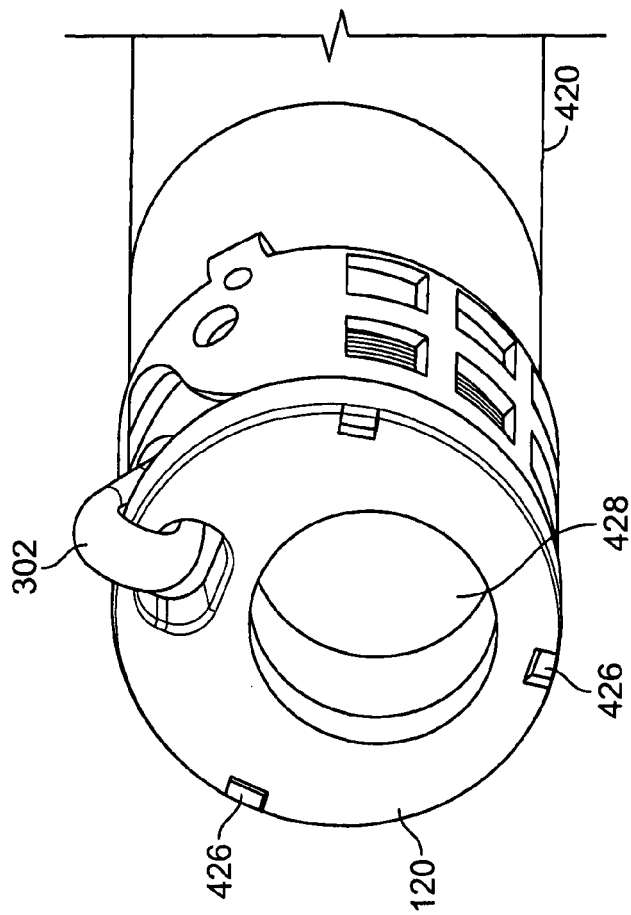
FIG. 4 is an enlarged but still simplified perspective or isometric view of a portion of what is shown in FIG. 3.

FIG. 3 shows illustrative instrumentation 400 for delivering distal collar structure 120 into the coronary sinus of a patient. FIG. 4 shows illustrative, releasable attachment of collar structure 120 on the distal end of instrumentation 400. Instrumentation 400 includes proximal handle and actuator components 410 (which always remain outside the body of the patient), and elongated, catheter-like, distal components 420 (which are insertable into blood vessels of the patient to reach the patient's right atrium and ultimately the coronary sinus). Extreme distal portions 422 and 424 may have the ability to achieve the depicted curvature(s), which facilitate getting the structure into the coronary sinus and aiming the distal end toward particular tissue structures into which it is desired for anchor 110 to be driven. In particular, catheter system 400 is preferably steerable, with handle component 412 being rotatable relative to main handle component 410 to activate an articulating tip on the distal end of the catheter. The compound curve of portions 422 and 424 facilitates access to the coronary sinus and aides in positioning of the distal anchor. FIG. 4 shows collar 120 being releasably held on the distal end of instrumentation 400 by snap-fit tabs 426. FIG. 4 also shows how the distal end 302 of tether 300 loops through an aperture in collar 120 to secure those two elements together. Catheter 420 has two parallel lumens. A smaller side lumen is the one through which tether structure 300 passes. The larger main lumen 428 is used later for passage therethrough of instrumentation for delivering and driving anchor 110.

Figure 5:
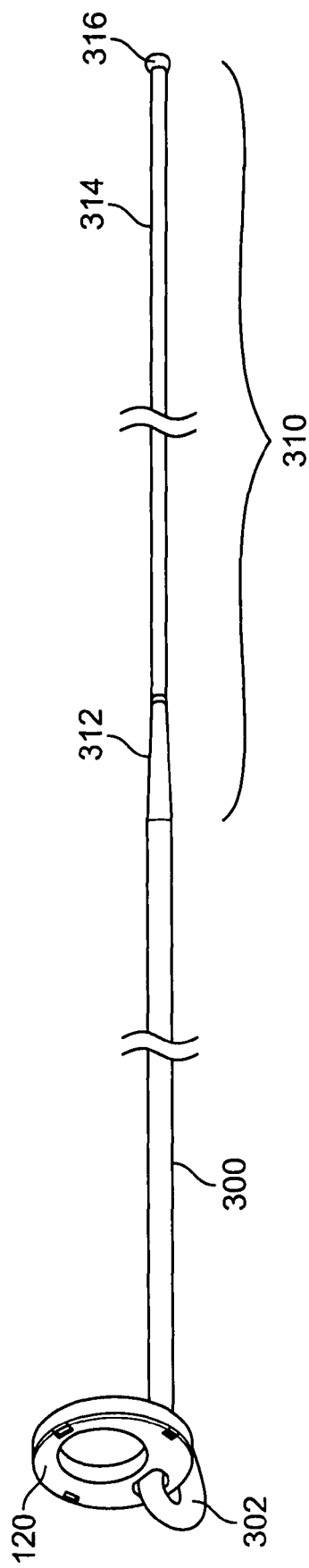
FIG. 5 is a simplified elevational view of an illustrative embodiment of some apparatus that may be constructed in accordance with the invention.

FIG. 5 shows an illustrative embodiment of distal collar structure 120 together with tether 300, and with a proximal extension 310 of the tether. Whereas tether 300 can be made of braided polyester cord, the major portion 314 of proximal extension can be made of catheter guide wire material such as nitinol wire. The implant cord can be spliced on itself to retain collar 120. The implant cord can be reflowed onto the nitinol guidewire in region 312, thereby maintaining a low profile and high tensile strength in the transition from polyester cord to nitinol wire. Note that the proximal end of guide wire 314 remains outside the patient at all times. The nitinol guidewire can therefore be used to facilitate rapid exchange of various delivery catheters. The proximal end of guide wire 314 may include a small rounded bead or ball 316 to facilitate smooth introduction of other apparatus over guide wire 314. The implant cord is preferably a braided bi-component polyester, meaning that the yarns have a core material that is coated with another material. These two materials may be chemically the same. However they are processed such that the melt temperature of the two is different. During reflow, the outer coating melts, but the core yarn does not. This yields desirable properties such as high tensile strength, open porosity, yarn-to-yarn adhesion, and yarn-to-nitinol adhesion. This prevents braids from splaying or coming apart. It also provides extra strength to splice joints and reflow joints.

Figure 6:
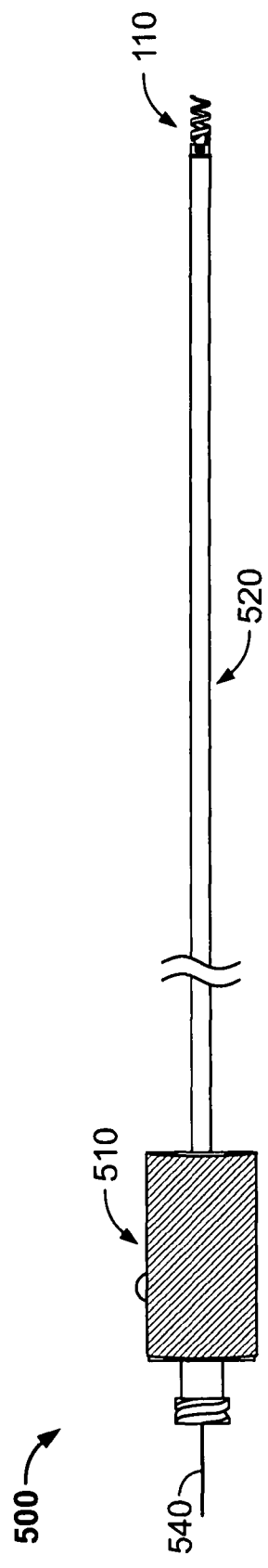
FIG. 6 is a simplified elevational view of an illustrative embodiment of some additional instrumentation and apparatus in accordance with the invention.
Figure 7:
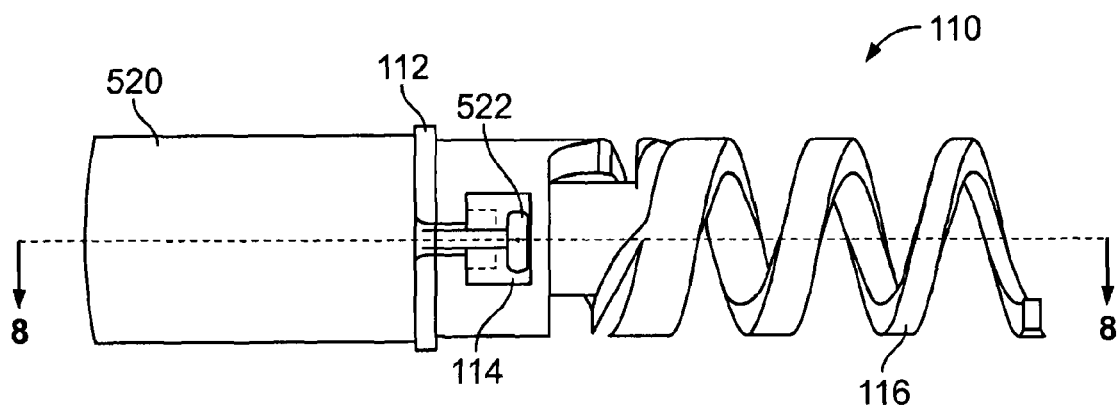
FIG. 7 is an enlarged but still simplified elevational view of a portion of what is shown in FIG. 6.
Figure 8:
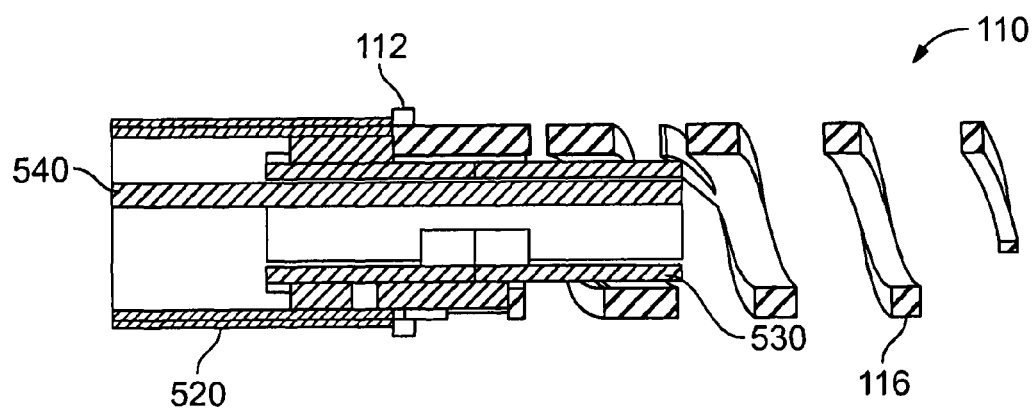
FIG. 8 is a simplified sectional view of what is shown in FIG. 7.

FIG. 6 shows an illustrative embodiment of apparatus 500 that can be used to deliver distal anchor 110 into the patient, through distal collar 120, and into tissue of the patient beneath collar 120. This is done via the main lumen 428 of instrumentation 400, which is still in place in the patient at this time. Instrumentation 500 includes a proximal handle/actuator portion 510, which always remains outside the patient. Instrumentation 500 further includes a distal, catheter-like portion 520, to which anchor 110 is releasably attached at the extreme distal end. FIG. 7 shows details of the releasable attachment of anchor 110 to structure 520. FIG. 8 shows some interior components of this apparatus. As can be seen in these FIGS., anchor 110 is held on the end of structure 520 by T-shaped projections 522 from structure 520 into C-shaped recesses 114 in the head region of anchor 110. Anchor 110 is basically hollow and cylinder-like, but with a hollow, helical thread portion 116 extending in the distal direction. Inside anchor 110 is another cylindrical member or tube 530, to which a wire 540 is attached. Cylinder 530 is relatively short and is axially movable relative to anchor 110. Wire 540 extends from cylinder 530 in the proximal direction all the way out of the patient (see FIG. 6). Projections 522 are resiliently biased to deflect radially inwardly out of recesses 114. This inward deflection of projections 522 is initially prevented by the presence of cylinder 530 inside anchor 110 adjacent to projections 522. Note that with projections 522 in recesses 114, torque can be transmitted from instrumentation 500 to anchor 110 to drive the anchor into tissue. As anchor 110 goes into tissue, tissue inside the hollow anchor gradually pushes cylinder 530 in the proximal direction relative to the anchor. This shifting of cylinder 530 can be viewed (e.g., radiologically) as an indication that anchor 110 is successfully penetrating tissue or has successfully penetrated tissue to the desired degree. Proximal shifting of cylinder 530 also increases the proximal projection of the proximal end of wire 540 from the rest of instrumentation 500. This can be another way that penetration of tissue by anchor 110 can be monitored.

When anchor 110 has penetrated tissue to the desired degree, wire 540 can be used to pull cylinder 530 proximally even farther. In particular, cylinder 530 can now be pulled proximally beyond the vicinity of projections 522. This allows projections 522 to deflect radially inward, thereby releasing anchor 110 from instrumentation 500.

The drive shaft 520 for driving anchor 110 is preferably extremely flexible and able to transmit torque to allow the rotation of anchor 110 into tissue through a tortuous path. This can be accomplished through the use of very dense or high pic count braid and coil structures in the construction of the shaft. As has been said, drive shaft 520 fits inside the steerable delivery catheter 400 used for placement of collar 120. Engagement members 522 can be made of a highly elastic (possibly shape-memory) material such as nitinol. Indicator 530 can be made of a dense material such as platinum.

After anchor 110 has been driven and released from instrumentation 500, that instrumentation can be pulled out of the patient. Another elongated member (not shown) can then be inserted through lumen 428 to push anchor 110 and collar 120 off the distal end of instrumentation 400. That pusher and instrumentation 400 can then be pulled proximally out of the patient.

Figure 9:
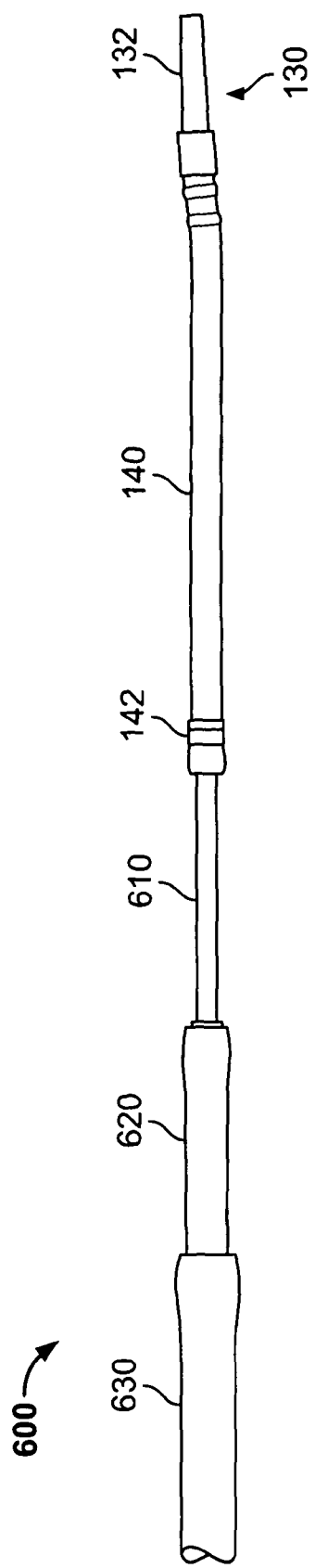
FIG. 9 is a simplified elevational view of an illustrative embodiment of some additional instrumentation and apparatus in accordance with the invention.

FIG. 9 shows the distal portion of illustrative instrumentation 600 for delivering distal bushing 130 and sleeve 140 into the patient. Instrumentation 600 includes three concentric catheter-like elements 610, 620, and 630. Elements 610, 620, and 630 are all slidable axially relative to one another. Innermost catheter 610 is a hollow tube that fits loosely around tether 300. Accordingly, instrumentation 600, with elements 130 and 140 loaded into it, can be passed into the patient by using the tether structure like a guide wire. The distal portion of catheter 610 passes coaxially through sleeve 140 and into bushing 130 with a relatively loose fit. The distal end of catheter 620 remains proximal of the proximal end of sleeve 140 and can be used to abut the proximal end of the sleeve. The distal end of catheter 630 initially fits over everything else that is shown in FIG. 9.

As the distal end of the FIG. 9 apparatus approaches already-implanted distal anchor 110 and collar 120 (i.e., by passing along tether structure 300), outer catheter 620 may be pulled back proximally to expose the extreme distal portion 132 of bushing 130. This allows that portion of bushing 130 to pass through the aperture 124 in collar 120 (see FIGS. 1 and 2). Inner catheter 610 should also not extend so far into bushing 120 at this time that it interferes with entry of bushing portion 132 through aperture 124.

After bushing portion 132 has reached the condition relative to collar 120 that is shown in FIGS. 1 and 2, catheter 610, 620, and 630 can be shifted axially relative to one another to push elements 130 and 140 off of catheter 610 and out of catheter 630. Basically this is done by pushing distally on catheter 620 and proximally retracting catheters 610 and 630. During this procedure, the distal end of catheter 620 abuts the proximal end of sleeve 140 and keeps elements 130 and 140 in place while catheters 610 and 630 are being proximally withdrawn. After elements 130 and 140 are thus off and out of instrumentation 600, that instrumentation can be withdrawn from the patient.

As was mentioned earlier, sleeve 140 is preferably a member that reduces possible stress on the tissue adjacent to the implant cord 300 by increasing the surface area and distributing the load over a larger area. Sleeve 140 can be constructed in many ways, including but not limited to: surgical pledget cloth, tubing sections made from metal or polymers, or braided structures of metal or polymers. The presently preferred practice includes a loosely woven structure that shortens and increases in diameter as it is compressed. This structure allows for easy delivery and maintains total coverage of implant cord 300 through a range of cinch distances.

Figure 10:
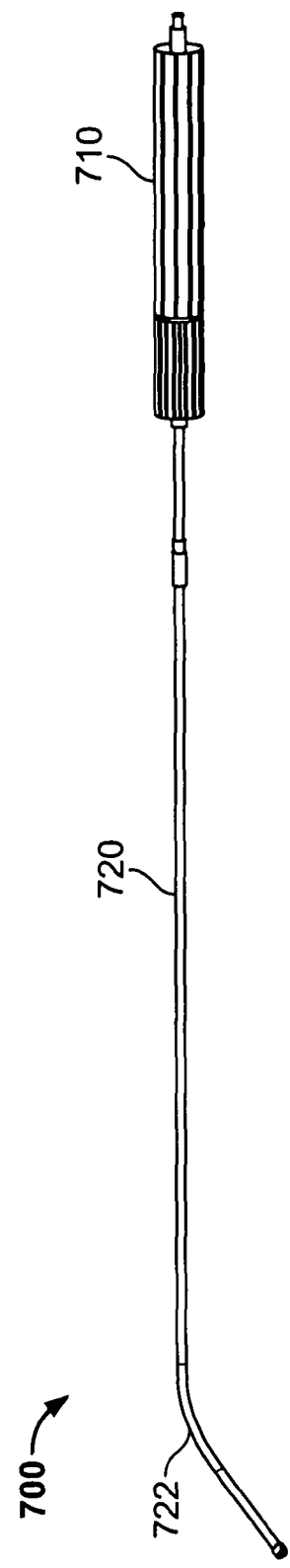
FIG. 10 is a simplified elevational view of an illustrative embodiment of some further instrumentation and apparatus in accordance with the invention.
Figure 11:
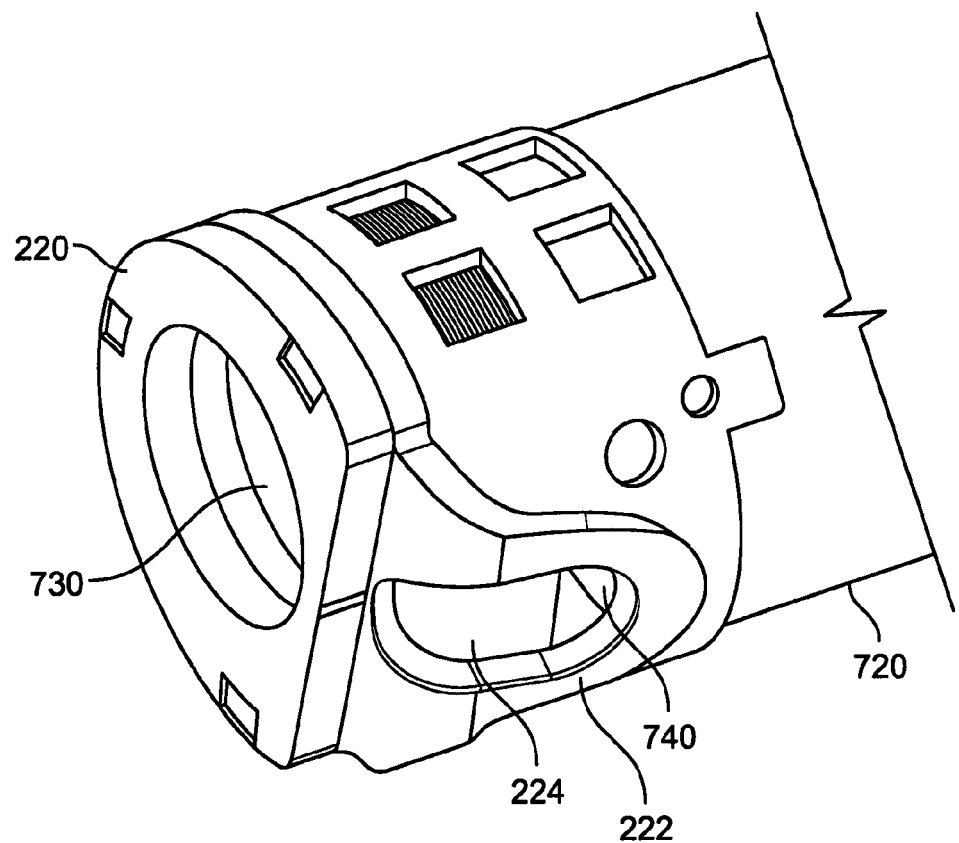
FIG. 11 is an enlarged but still simplified perspective or isometric view of a portion of what is shown in FIG. 10.

The next step is to deliver and implant proximal anchor 210 and collar 220. Illustrative instrumentation 700 for delivering collar 220 into the patient is shown in FIGS. 10 and 11. Instrumentation 700 can be somewhat like above-described instrumentation 400, and so the description of instrumentation 700 can be somewhat abbreviated. Instrumentation 700 has a main lumen 730, via which anchor 210 will be later delivered, and a side lumen 740 that is the lumen through which the proximal portion of tether structure 300 passes. The proximal portion of tether structure 300 also passes through the aperture 224 in collar 220. Collar 220 can be releasably (e.g., snap-fit) retained on the distal end of instrumentation 700 in the same way that collar 120 is releasably retained on the distal end of instrumentation 400. Instrumentation 700 is preferably another steerable delivery system. For example, this system may have an articulating distal tip 722 inside of a telescoping passive curve that allows for positioning the proximal collar 220 and later the proximal anchor 210. Thus the distal portion 722 of instrumentation 700 may be capable of achieving a curvature like that shown in FIG. 10 to facilitate positioning against tissue at a desired location in the patient. For example, this may be a particular location on the wall of the right atrium outside the ostium of the coronary sinus.

When collar 220 on instrumentation 700 is in the patient against tissue at the desired location, proximal anchor 210 may be delivered into the patient via the main lumen 730 of instrumentation 700. This may be done using another instance of instrumentation like that shown in FIGS. 6-8 (but with anchor-feature reference numbers 110, 112, 114, and 116 changed to 210, 212, 214, and 216, respectively, to account for the fact that the apparatus is now being used for proximal anchor 210 rather than distal anchor 110). In this way, proximal anchor 210 is driven through collar 220 and rotationally threaded into the patient's tissue at the desired location.

After anchor 210 has been driven as described above, it is released from the instrumentation that was used to deliver and drive it, and that instrumentation can be withdrawn from the patient. Anchor 210 and collar 220 can be released from instrumentation 700 in a manner similar to the release of anchor 110 and collar 120 from instrumentation 400. Instrumentation 700 can then also be withdrawn from the patient.

Figure 12:
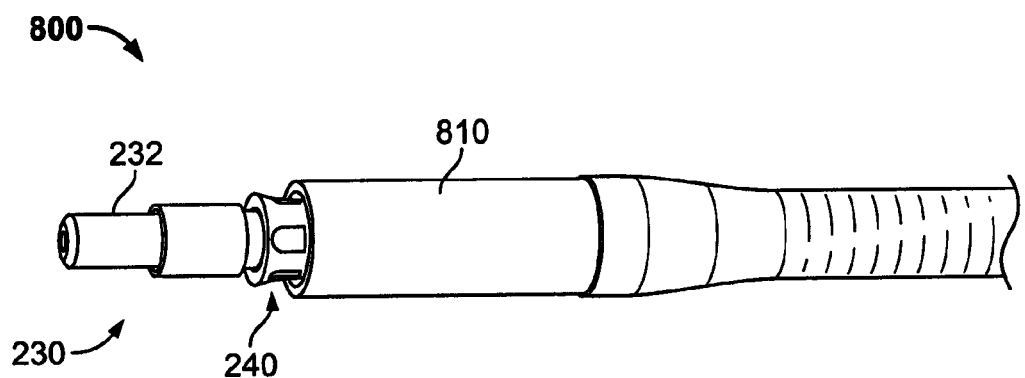
FIG. 12 is a simplified perspective or isometric view of an illustrative embodiment of some further instrumentation and apparatus in accordance with the invention.
Figure 13:
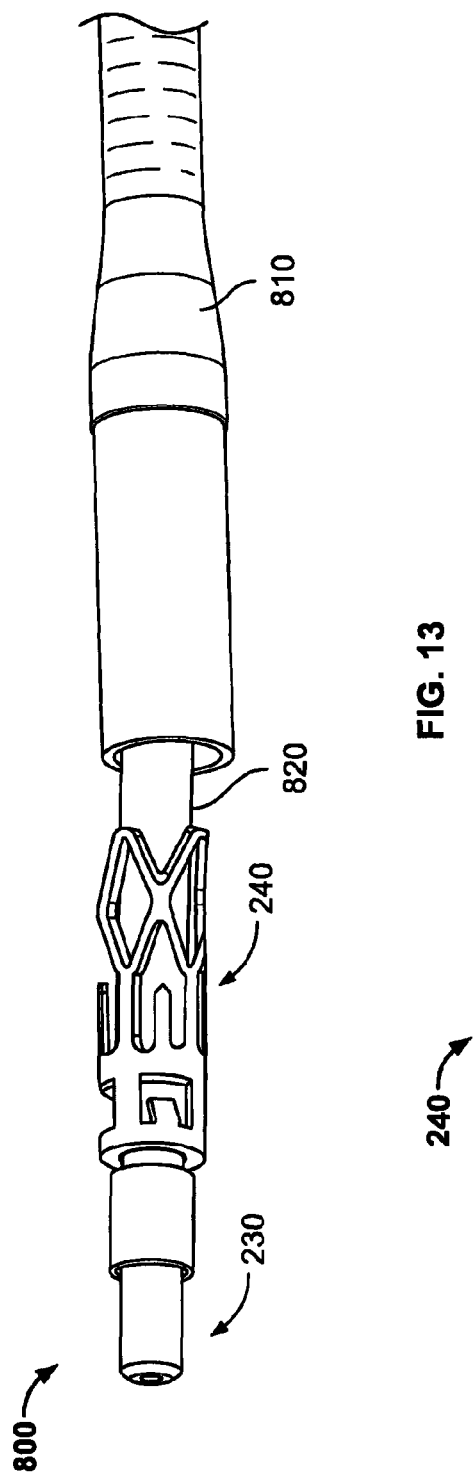
FIG. 13 is similar to FIG. 12, but shows the instrumentation in a different operating condition.

The next step is to deliver proximal bushing 230 and cinch 240 into the patient. FIG. 12 shows an illustrative embodiment of instrumentation 800 for doing this. In particular, instrumentation 800 has a catheter-like distal portion in which bushing 230 and cinch 240 are loaded. This apparatus is fed into the patient with the proximal portion of tether structure 300 passing through the center of elements 230, 240, and 800. When bushing 230 reaches collar 220, the distal portion 232 of the bushing passes through the aperture 224 in the collar as shown in FIGS. 1 and 2. The distal end of an outer catheter 810 of instrumentation 800 may be retracted proximally sufficiently to permit this (e.g., as in FIG. 12). The portions 244 and 246 of cinch 240 that are resiliently biased to deflect inwardly (as described earlier in this specification) are prevented from doing so by virtue of the fact that the cinch is initially disposed around an inner catheter structure 820 of instrumentation 800 (see FIG. 13). The distal end of inner catheter 820 may also abut the proximal end of bushing 230 at this time.

It is now possible to change or adjust the spacing between implanted tissue anchor structures 100 and 200. For example, this spacing can be reduced by pulling proximally on the proximal end of tether structure 300 while pushing distally on inner catheter 820, or by any other combination of manipulations of these elements that causes inner catheter 820 to move distally relative to tether structure 300. Because distal tissue anchor 100 is secured to tether 300, and proximal tissue anchor 200 can be pushed in the distal direction relative to anchor 100 by inner catheter 820, the distance between anchors 100 and 200 can be decreased by the above-described relative motions of elements 300 and 820. If, after anchors 100 and 200 have been moved toward one another, it is found that they are too close, some or all of their movement toward one another can be undone by simply removing some or all of the force that was used to move them together. The natural resilience of the tissue will cause them to move apart again. Adjustments of this kind can be made until the desired effect on the tissue is achieved. (Cinch 240 is, of course, not yet in engagement with tether 300, and so it does not yet inhibit motion of anchors 100 and 200 either toward or away from one another at this time.)

Figure 14:
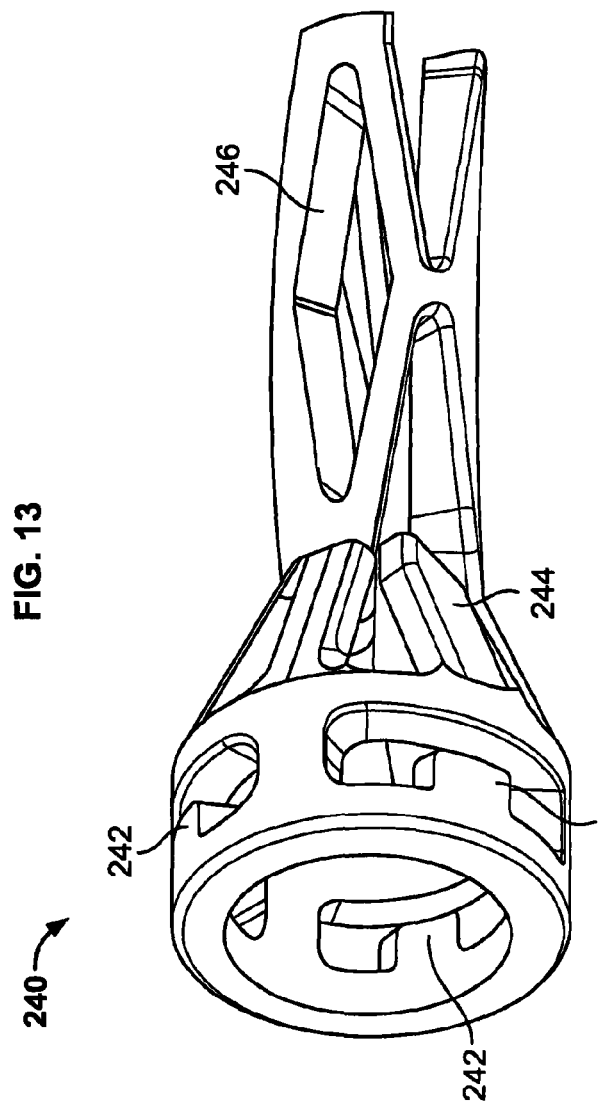
FIG. 14 is a simplified perspective or isometric view of one component of the apparatus shown in FIG. 13 in a different operating condition.

When implanted tissue anchors 100 and 200 are at the desired spacing from one another, cinch 240 can be deployed onto tether 300 to permanently maintain that spacing. This can be done by pulling back on catheter 820, while holding cinch 240 in position by means of another catheter (not visible in FIG. 13). This other catheter is concentrically disposed between catheters 810 and 820, and its distal end abuts the proximal end of cinch 240 during its use to hold cinch 240 in position as described in the preceding sentence. The condition of cinch 240 after it has thus been removed from catheter 240 is shown in FIG. 14. (FIG. 14 shows only deployed cinch 240, and omits tether 300, which, of course, passes coaxially through the center of the cinch and is now engaged by the cinch.) Cinch 240 is resiliently biased to go to the FIG. 14 condition. It will be apparent from FIG. 14 how deployed cinch 240 engages the tether 300 that passes coaxially through it. Details of this engagement are described earlier in this specification. Cinch 240 can be made of any suitable, highly elastic and/or shape-memory material such as nitinol.

Figure 15:
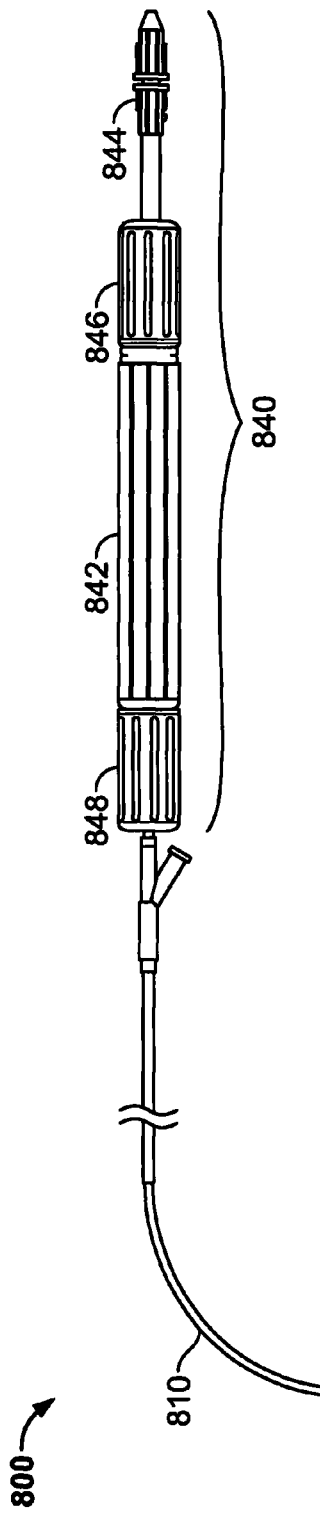
FIG. 15 is a simplified elevational view of an illustrative embodiment of more of the instrumentation that is shown only in part in FIGS. 12 and 13.

FIG. 15 shows additional aspects of an illustrative construction of instrumentation 800 that can be provided to facilitate the operations that have just been described. The handle portion 840 (which always remains outside the patient's body) includes a main portion 842 and three separately rotatable actuators 844, 846, and 848. Actuator 844 is rotatable to selectively lock component 845 onto an adjacent portion of tether structure 300. After that locking connection has been made, actuator 846 can be rotated to selectively shift component 845 (and therefore tether structure 300) in the proximal direction. (Such proximal motion can be wholly or partly undone, if desired, by rotating actuator 846 in the opposite direction.) The amount of motion of tether 300 can be observed by observing the change in distance between actuators 844 and 846 (i.e., the length of component 845 that is exposed). When the desired spacing between anchor structure 100 and 200 has been achieved, actuator 848 can be rotated to retract catheter 820 and thereby deploy cinch 240 onto tether structure 300.

After cinch structure 240 has been deployed onto tether 300 as described above, the grip of instrumentation 800 on the tether structure can be released (by appropriate rotation of actuator 844), and instrumentation 800 can be removed from the patient.

Figure 16:
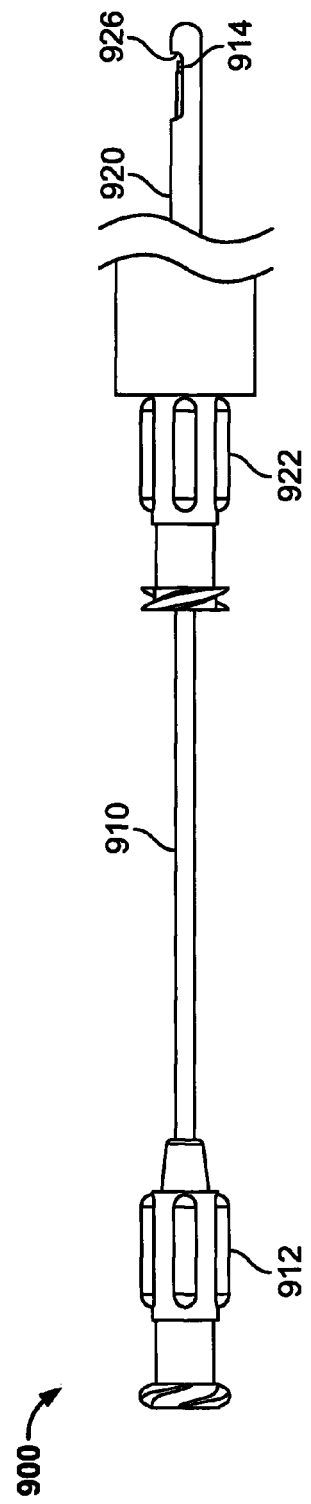
FIG. 16 is a simplified elevational view of an illustrative embodiment of still more instrumentation in accordance with the invention.
Figure 17:
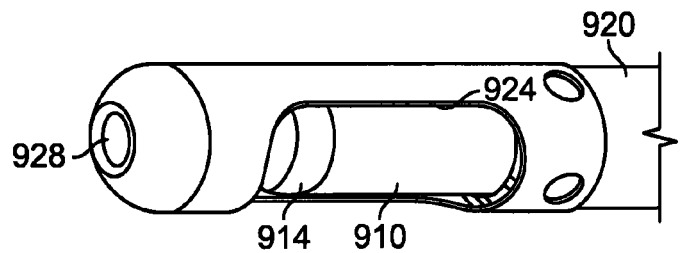
FIG. 17 is an enlarged but still simplified perspective or isometric view of a portion of what is shown in FIG. 16.

The next step is to sever the excess of tether structure 300 that is proximal of cinch structure 240 and to remove that excess tether structure from the patient. FIGS. 16 and 17 show an illustrative embodiment of instrumentation 900 for doing this. Instrumentation 900 includes an inner catheter-like component 910 and an outer catheter-like component 920. These two catheter-like components are axially slidable relative to one another, and each has a proximal handle portion (912 and 922, respectively) that remains outside the patient's body at all times. The distal end of inner catheter 910 is sharpened to produce a circular cutter blade 914. The distal portion of outer catheter 920 has an opening 924 on one of its sides. Distally beyond cutter blade 912 and aperture 924, outer catheter 920 provides an anvil surface 926 that faces toward cutter blade 914.

To use instrumentation 900, outer catheter 920 is first inserted into the patient along tether structure 300. Tether structure 300 can be routed in either of two ways relative to outer catheter 920. One possible routing is for the tether structure to enter the distal-most opening 928 in outer catheter 920, to come out of side opening 924, and to then pass along the outside of the proximal remainder of catheter 920. The other possible routing is for tether structure 300 to pass along the outside of the extreme distal portion of catheter 920, to enter side opening 924, and to then pass along the inside of the proximal remainder of catheter 920.

After catheter 920 has been inserted into the patient until its distal end is at the desired location proximal of cinch structure 240, inner catheter 910 can be inserted into the outer catheter. If the latter of the above-mentioned routings of tether structure 300 has been used, then inner catheter 910 is inserted into outer catheter 920 around the tether structure. It will be apparent from the foregoing that either of the above-mentioned routings of tether structure 300 causes that structure to pass between cutter blade 914 and anvil surface 926. Accordingly, when cutter blade 914 is forced against the anvil surface (possibly with rotation of the cutter blade to facilitate cutting), cutter blade 914 cuts through tether structure 300 proximal of cinch structure 240. Instrumentation 900 and the portion of tether structure 300 proximal of the cut that has been made in it can now be withdrawn from the patient. This leaves behind in the patient only the implanted structure (basically what is shown in FIG. 2, but with cinch 240 collapsed onto tether 300).

Figure 18:
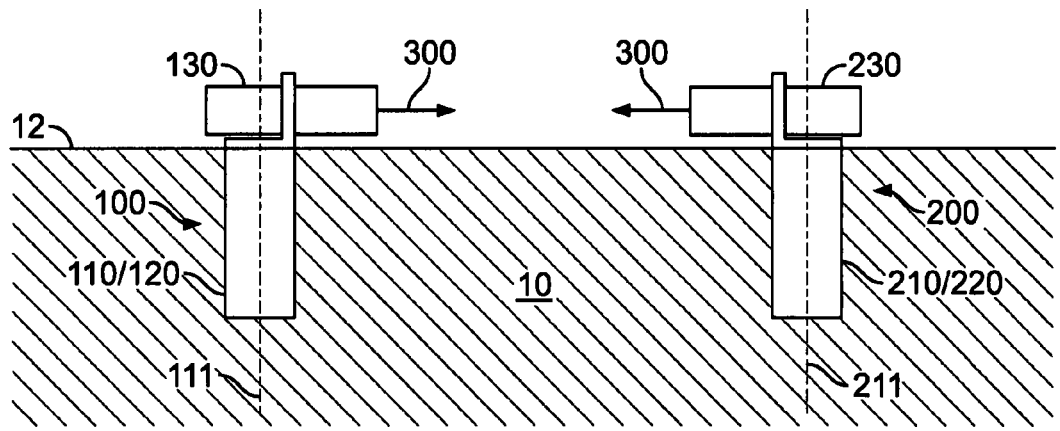
FIG. 18 is a simplified schematic diagram that is useful in explaining certain possible advantages of structures in accordance with the invention.
Figure 19:
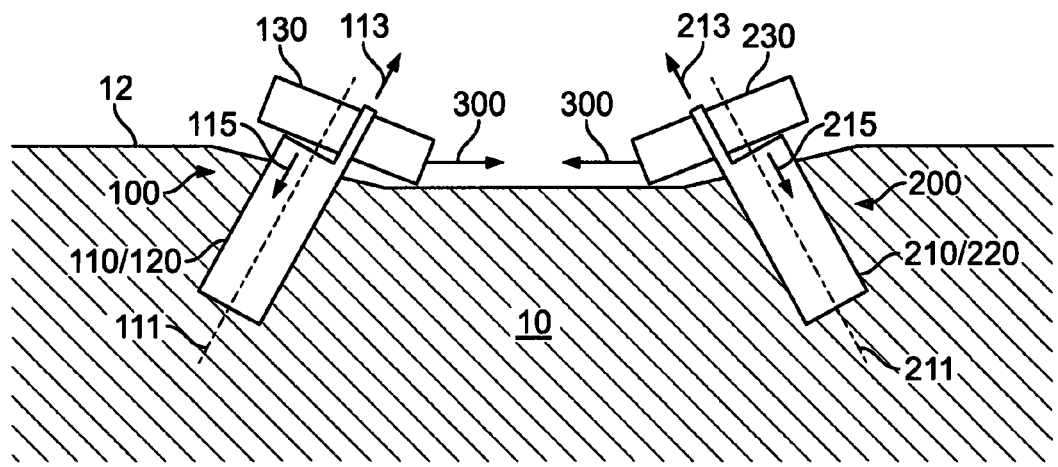
FIG. 19 is similar to FIG. 18, but shows another operating condition of what is shown in FIG. 18.

FIGS. 18 and 19 are provided to illustrate how aspects of the invention help to keep the longitudinal axes 111 and 211 of anchors 110 and 210 transverse to the longitudinal axis of tether 300 even when tether 300 is tensioned to pull anchors 110 and 210 together. The various elements shown in FIGS. 18 and 19 are greatly simplified, and indeed each anchor and its associated collar are combined into one element (e.g., 110/120 or 210/220). In FIG. 18 the arrows 300 indicate the force on each anchor structure 100 or 200 due to tension in the tether 300 between the anchor structures. Reference number 10 denotes the patient's body tissue into which anchor structures 100 and 200 have been driven (through the surface 12 of that tissue). FIG. 19 shows that the tendency of tether tension force 300 is to tip anchors 110 and 210 toward one another. However, FIG. 19 also shows that as this happens, each bushing 130 or 230 begins to exert a counteracting moment on the associated anchor. In the case of anchor 110, for example, this moment is due to the force couple 113/115 (force 113 pulling up on the side of anchor 110 toward tether 300, and force 115 pushing down on the side of anchor 110 remote from tether 300). While force 300 is trying to incline anchor 110 toward anchor 210, moment or force couple 113/115 is trying to tip anchor 110 back in the opposite direction. Accordingly, anchor 110 may incline somewhat toward anchor 210, but then oppositely directed moment 113/115 becomes great enough to prevent further tipping of the anchor. Although anchor 110 may not remain completely perpendicular to the longitudinal axis of tether 300, its longitudinal axis 111 does remain transverse to the tether axis. The above-described moment 113/115 helps prevent anchor 110 from responding to tether tension by becoming aligned with the tether axis. Anchor 110 is better at holding the tissue 10 (into which it was initially driven transverse to the tether axis) to the extent that it can remain transverse to the tether axis (and therefore the axis of tether tension). The structure of this invention helps anchor 110 remain transverse to the tether axis as described above. Anchor 210 behaves similarly in response to the similar force couple 213/215 acting on it as shown in FIG. 19.

Figure 20:
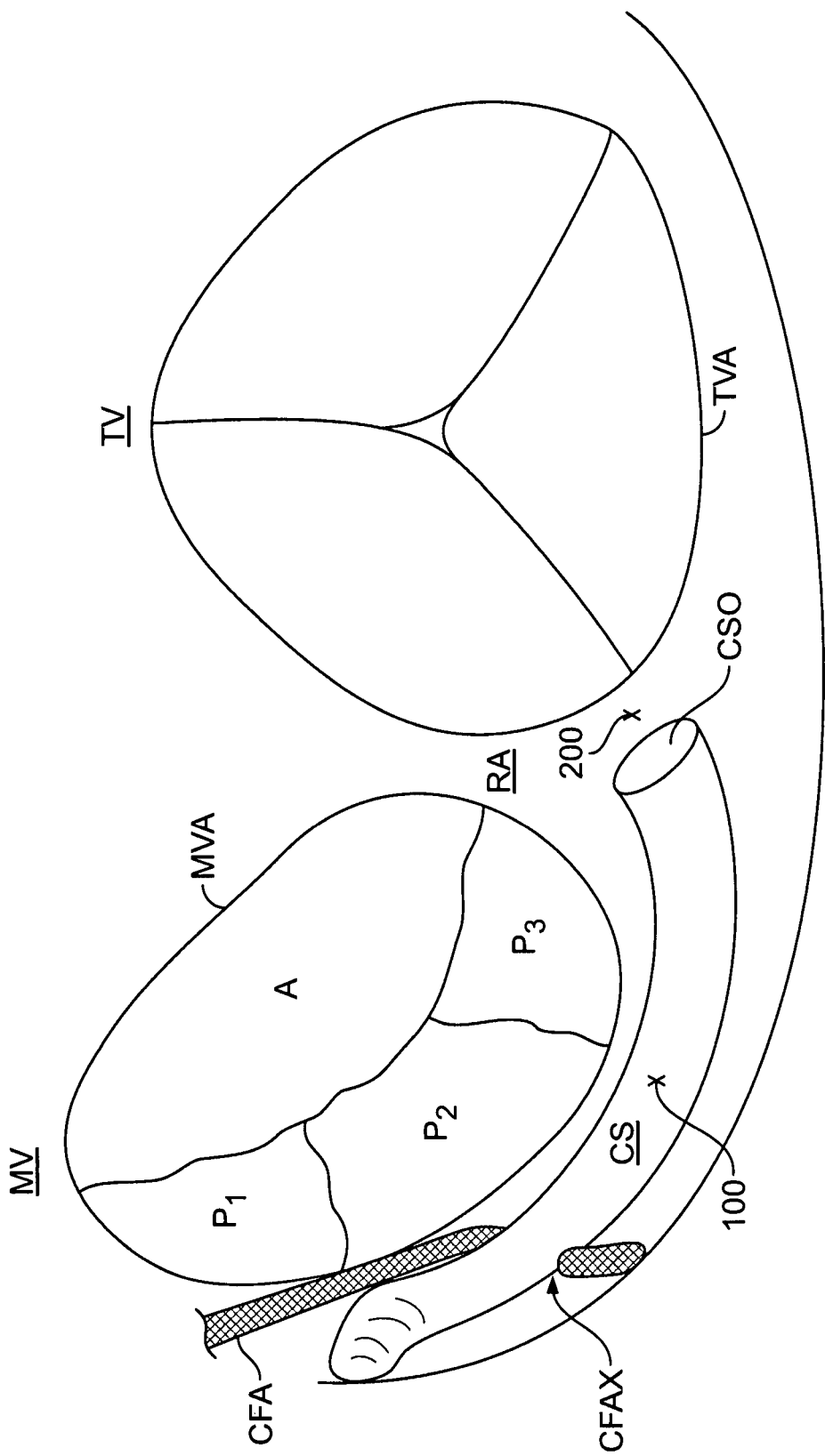
FIG. 20 is a schematic sectional view of a portion of a patient's heart that is useful in explaining certain possible aspects of the invention.

FIG. 20 is a schematic depiction of a section through a patient's heart at approximately the level of the mitral valve annulus (MVA) looking down on the leaflets of the mitral valve (MV), and also showing the right atrium (RA) and the tricuspid valve (TV). The leaflets of the mitral valve are the anterior leaflet A and the posterior leaflet having three portions P1, P2, and P3. FIG. 20 further shows the approximate locations of the coronary sinus ostium CSO; the right atrium RA outside the CSO; and the coronary sinus CS extending from the CSO, along the posterior side of the valve, and toward the P3 portion of the posterior valve leaflet. FIG. 20 still further shows the circumflex artery (CFA) and the approximate point CFAX at which the circumflex artery crosses under the coronary sinus CS. Also shown in FIG. 20 are approximate preferred locations for distal anchor 100 and proximal anchor 200. In particular, distal anchor 100 is preferably located in the coronary sinus proximal to the circumflex artery crossing CFAX. (Proximal to the circumflex artery crossing means between the CFAX and the coronary sinus ostium CSO.) This distal anchor location is preferred so that the implant of this invention does not have a constricting effect on the circumflex artery. Proximal anchor 200 is preferably located in the right atrium RA between the coronary sinus ostium CSO and the tricuspid valve annulus (TVA). Although not shown in FIG. 20, it will be understood that anchors 100 and 200 are connected together by the tether structure shown in earlier FIGS. Other considerations that can be applied to the location and/or orientation of anchors 100 and 200 are taught in the two prior patent applications that are mentioned earlier in this specification. For example, these other considerations may relate to what tissue the anchors are driven into and/or how the proximal anchor 200 is spaced or displaced from the approximate plane of the mitral valve annulus MVA.

The second of the two above-mentioned prior published patent applications shows embodiments in which four screw-type tissue anchor structures are used (instead of only two as in the embodiments that are the subject of FIGS. 1-17 herein). It will be appreciated that principles of the present invention are equally applicable to embodiments with more than two anchors (e.g., to four-anchor embodiments).

It will be understood that the foregoing is only illustrative of the principles of the invention, and that various modifications can be made by those skilled in the art without departing from the scope and spirit of the invention. For example, the particular shapes that are shown for various components are only illustrative in some respects, and other shapes can be used instead if desired. As another example of modifications within the scope of the invention, use of the invention to shorten a portion of the mitral valve annulus is only illustrative of how the invention can be used, and it can alternatively be applied to shortening the distance between two areas in soft body tissue at other locations inside a patient's body. For example, it may be usable inside a ventricle of a patient's heart to reshape the ventricle.

The invention claimed is:

1. A tissue anchor assembly for penetrating a surface of a tissue structure and thereafter being usable to apply a force to the tissue structure substantially parallel to the surface comprising:
   a rotatable anchor structure for entering the tissue substantially perpendicular to the surface;
   a collar structure rotatable around a head of the anchor structure and having an apertured section that stands up from the head of the anchor structure;
   a flexible tether member attached to the collar structure for use in applying force substantially parallel to the surface; and
   a substantially rigid bushing structure around a portion of the tether member and passing through an aperture in the apertured section for resisting any tendency of the anchor structure to tip toward axial alignment with the force applied by the tether member, the substantially rigid bushing structure including a distal portion having a smaller outer circumference than a proximal portion,
   wherein the proximal portion of the rigid bushing structure has a larger outer circumference than the aperture of the collar structure and the distal portion of the rigid bushing structure includes a longitudinal slot wide enough to permit the flexible tether member to extend laterally out of the bushing, the longitudinal slot being formed solely in the distal portion, the flexible tether member extends through the proximal portion, the proximal portion completely surrounding the tether member, the flexible tether member extends through the apertured section and laterally out of the longitudinal slot towards the rotatable anchor structure, and the flexible tether member is attached to the collar structure at or near the aperture section.

2. The assembly defined in claim 1 wherein the head extends above the collar structure, and wherein the collar structure includes a surface arranged to bear against a surface of the tissue structure, the apertured section of the collar structure extending above the head of the anchor structure, the apertured extension rotatable with the collar structure about a longitudinal axis of the anchor structure.

3. The assembly defined in claim 2 wherein the tether member is attached to the collar structure at a predetermined point around a periphery of the collar structure.

4. The assembly defined in claim 3 wherein the apertured section is adjacent the predetermined point.

5. The assembly defined in claim 4 wherein the bushing structure extends from adjacent the predetermined point substantially across the head of the anchor structure and in close proximity thereto.

6. The assembly defined in claim 1 further comprising:
   a sleeve member around the tether member and extending away from the bushing structure along the tether member.

7. The assembly defined in claim 6 wherein the sleeve member is connected to the bushing structure.

8. The assembly defined in claim 6 wherein the sleeve member fits loosely around the tether member.

9. The assembly defined in claim 8 wherein the sleeve member is elastically compressible lengthwise of the tether member.

10. The assembly defined in claim 6 further comprising:
    a radiologically visible marker on the sleeve member.

11. The tissue anchor assembly of claim 1, wherein the rotatable anchor structure includes a hollow helical thread portion having a hollow center that allows tissue to travel up through the hollow center during insertion of the rotatable anchor.

12. The tissue anchor assembly of claim 11, wherein the anchor structure includes at least one C-shaped recess that is sized to receive a T-shaped projection of a delivery apparatus.

13. The issue anchor assembly of claim 12, further comprising a cylindrical tube disposed within the rotatable anchor structure, the cylindrical tube being axially movable relative to the rotatable anchor structure.

14. A tissue anchor assembly for penetrating a surface of a tissue structure and thereafter being usable to apply a force to the tissue structure substantially parallel to the surface comprising:
   an anchor structure for entering the tissue substantially perpendicular to the surface;
   a collar structure around a head of the anchor structure and having an apertured section that stands up from the head of the anchor structure;
   a substantially rigid bushing structure insertable part way through an aperture in the apertured section, the substantially rigid bushing structure including a distal portion having a smaller outer circumference than a proximal portion;
   a tether member passing through the bushing structure;
   and a cinch structure for selectively engaging the tether member and thereby transmitting force substantially parallel to the surface from the tether member to the bushing, collar, and anchor structures, engagement of the bushing structure and the aperture resisting any tendency of the anchor structure to tip toward alignment with the force applied by the tether member,
   wherein the proximal portion of the rigid bushing structure has a larger outer circumference than the aperture of the collar structure and the distal portion of the rigid bushing structure includes a longitudinal slot wide enough to permit the tether member to extend laterally out of the bushing, the longitudinal slot being formed solely in the distal portion, the proximal portion completely surrounds the tether member, the tether member extends through the proximal portion, through the apertured section, and laterally out of the longitudinal slot towards the anchor structure, the tether member being attached to the collar structure at or near the aperture section.

15. The assembly defined in claim 14 wherein the collar structure is rotatable about a longitudinal axis of the anchor structure.

16. The assembly defined in claim 14 wherein the bushing structure extends across a head of the anchor structure and in close proximity thereto.

17. The assembly defined in claim 14 wherein the cinch structure is connected to the bushing structure.

18. The assembly defined in claim 14 wherein, in use, the tether member extends from the cinch structure, through the bushing structure, to another tissue anchorage that is spaced along the surface from the tissue anchor structure.

19. The assembly defined in claim 18 wherein the tether member is surrounded by a compressible resilient sleeve structure.

20. The assembly defined in claim 19 wherein the sleeve structure fits loosely around the tether structure.

21. The assembly defined in claim 20 wherein the sleeve structure has a length that elastically conforms to changes in spacing between the tissue anchor structure and the tissue anchorage, whereby the sleeve structure substantially always covers substantially the entire tether member between the tissue anchor structure and the tissue anchorage.

22. The assembly defined in claim 19 further comprising:
a radiologically visible marker on the sleeve structure.

23. A device for altering the length of a section of the annulus of a mitral valve comprising:
- a first rotatable tissue anchor sized for placement at a first point along the annulus;
- a second rotatable tissue anchor sized for placement at a second point along the annulus;
- each of the tissue anchors including a head;
- a collar rotatably mounted to each of the tissue anchors, each collar including an upwardly extending flange having an aperture disposed above the head;
- a first and second rigid bushing, each rigid bushing sized to extend through the aperture in the flange of a corresponding one of the collars, at least one of the first and second rigid bushings including a distal portion having a smaller outer circumference than a proximal portion;
- a tether having a first portion extending through the first rigid bushing and operatively coupled to the collar of the first tissue anchor, the tether having a second portion extending through the second rigid bushing;
- a sleeve disposed around the tether between the first and second tissue anchors and arranged to bear against the first and second bushings; and
- a cinch adjustably coupled to the second portion of the of the tether and arranged to maintain a tensile force on the tether, thereby maintaining a compressive force on the sleeve,
- wherein the sleeve is elastic in an axial direction, the proximal portion of the first rigid bushing has a larger outer circumference than the aperture of the collar, the distal portion of the first rigid bushing includes a longitudinal slot wide enough to permit the tether member to extend laterally out of the at least one of the first and second bushing, the longitudinal slot being formed solely in the distal portion, the proximal portion completely surrounds the tether, the tether extends through the proximal portion of the first rigid bushing, through the aperture, and laterally out of the longitudinal slot towards the collar, and the tether is attached to the collar at or near the aperture.

24. The device of claim 23, wherein the cinch is disposed proximally of the second tissue anchor, and wherein the first and second bushings each include an extended portion disposed between the first and second tissue anchors, and wherein the sleeve is resilient and fits over the extended portion of each of the first and second bushings.

* * * * *

UNITED STATES PATENT AND TRADEMARK OFFICE
CERTIFICATE OF CORRECTION

PATENT NO.         : 9,101,338 B2                                                    Page 1 of 1
APPLICATION NO.    : 11/800363
DATED              : August 11, 2015
INVENTOR(S)        : Paul J. Hindrichs et al.

It is certified that error appears in the above-identified patent and that said Letters Patent is hereby corrected as shown below:

<u>On the Title page</u>

<u>Item 75</u>

Line 2, "Steven D Kruse," should be -- Steven D. Kruse, --.

Line 3, "Todd A Krinke," should be -- Todd A. Krinke, --.

<u>Item 74</u>

Line 1, "Marshall Gerstein" should be -- Marshall, Gerstein --.

<u>In the Claims</u>

At Column 14, line 11, "issue" should be -- tissue --.

Signed and Sealed this
Fifteenth Day of March, 2016

Michelle K. Lee
*Director of the United States Patent and Trademark Office*